(12) United States Patent
Gerlach et al.

(10) Patent No.: US 6,835,293 B2
(45) Date of Patent: Dec. 28, 2004

(54) ANALYSIS SYSTEM

(75) Inventors: Andreas Gerlach, Karlsruhe (DE);
Günther Knebel, Nürtingen (DE)

(73) Assignee: Greiner Bio-One GmbH, Frickenhausen (DE)

( * ) Notice: Subject to any disclaimer, the term of this patent is extended or adjusted under 35 U.S.C. 154(b) by 292 days.

(21) Appl. No.: 09/901,467

(22) Filed: Jul. 9, 2001

(65) Prior Publication Data
US 2003/0006141 A1 Jan. 9, 2003

(51) Int. Cl.[7] .......................... G01N 27/453; B01L 3/00
(52) U.S. Cl. ...................... 204/600; 204/601; 422/100
(58) Field of Search ................. 204/450, 451, 204/600, 601; 422/68.1, 100, 101

(56) References Cited

U.S. PATENT DOCUMENTS 5,585,069 A * 12/1996 Zanzucchi et al. .......... 422/100
5,989,402 A * 11/1999 Chow et al. ................ 204/601
6,086,825 A *  7/2000 Sundberg et al. ........... 422/100
6,623,860 B2 *  9/2003 Hu et al. .................. 428/411.1

FOREIGN PATENT DOCUMENTS

WO    WO98/45693    10/1998
WO    WO 0002038     1/2000

* cited by examiner

*Primary Examiner*—Kaj K. Olsen
(74) *Attorney, Agent, or Firm*—Collard & Roe, P.C.

(57) ABSTRACT

The invention relates to an analysis system comprising a main body (1) with a surface, at least one analysis unit (6) consisting of at least two reservoirs (10) placed in flow connection by at least one passage (13, 14) being provided in the main body (1). Two electrical conductors (23, 24) are provided in the main body (1) or on the surface, a first respective end region thereof being connected respectively to one of the at least two reservoirs (10) and a respective second end region of the conductors (23, 24) being connected to or constituting a contact point (9) on the surface of the main body (1).

18 Claims, 10 Drawing Sheets

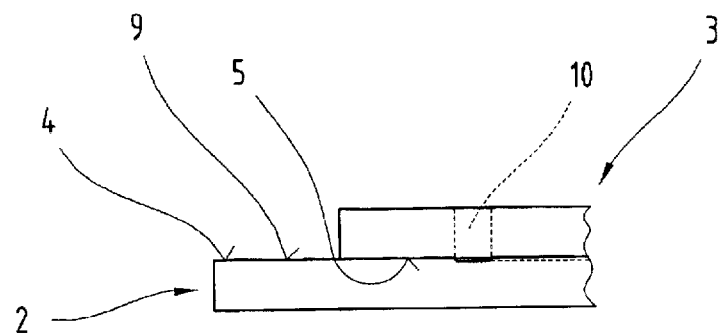
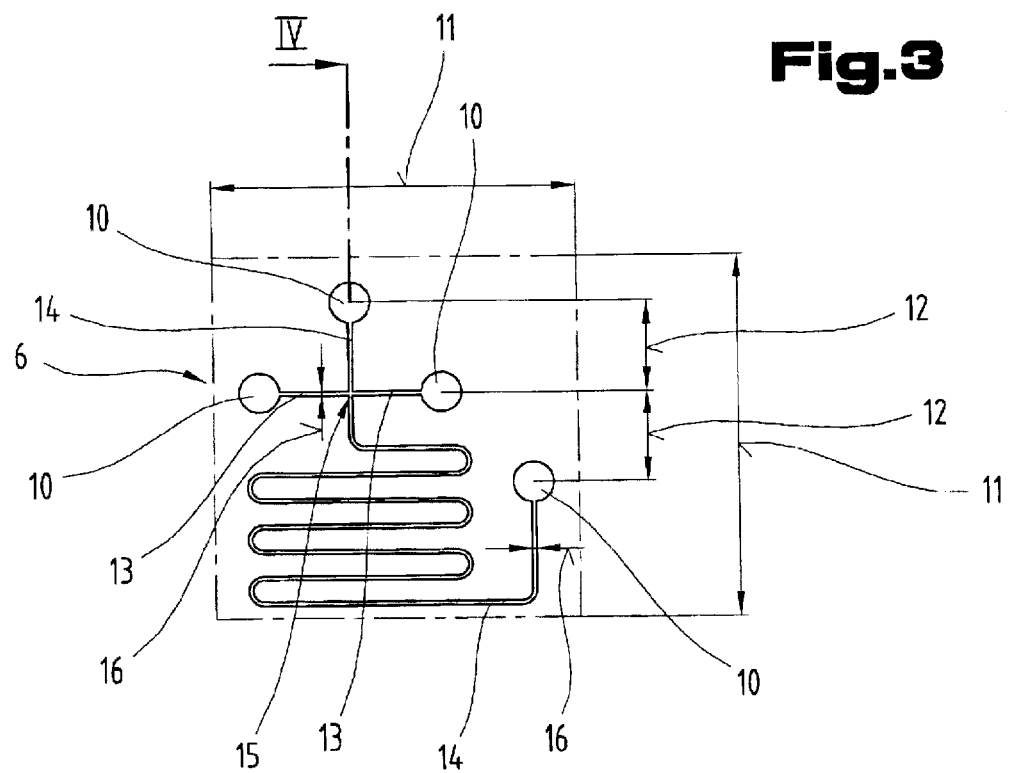

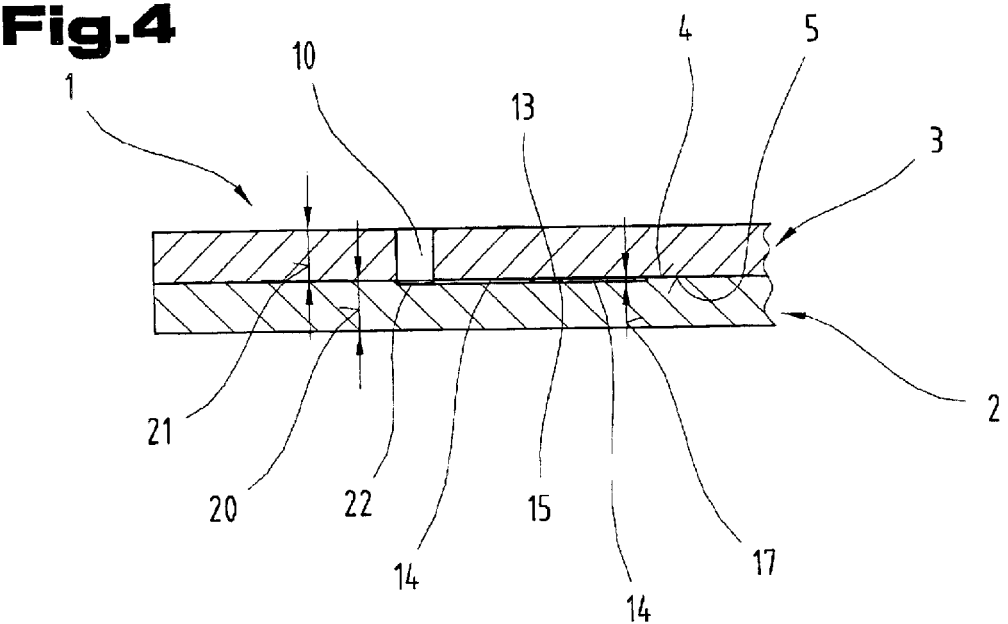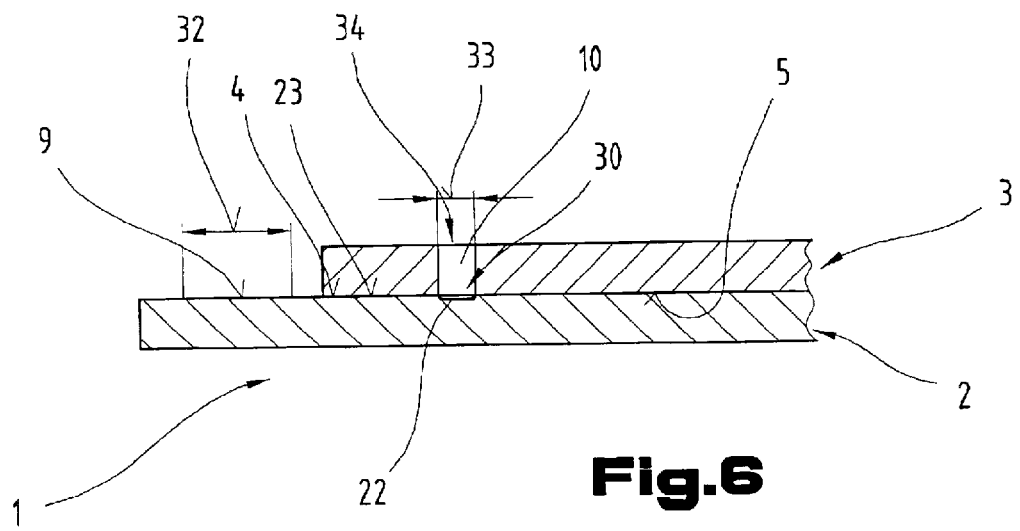

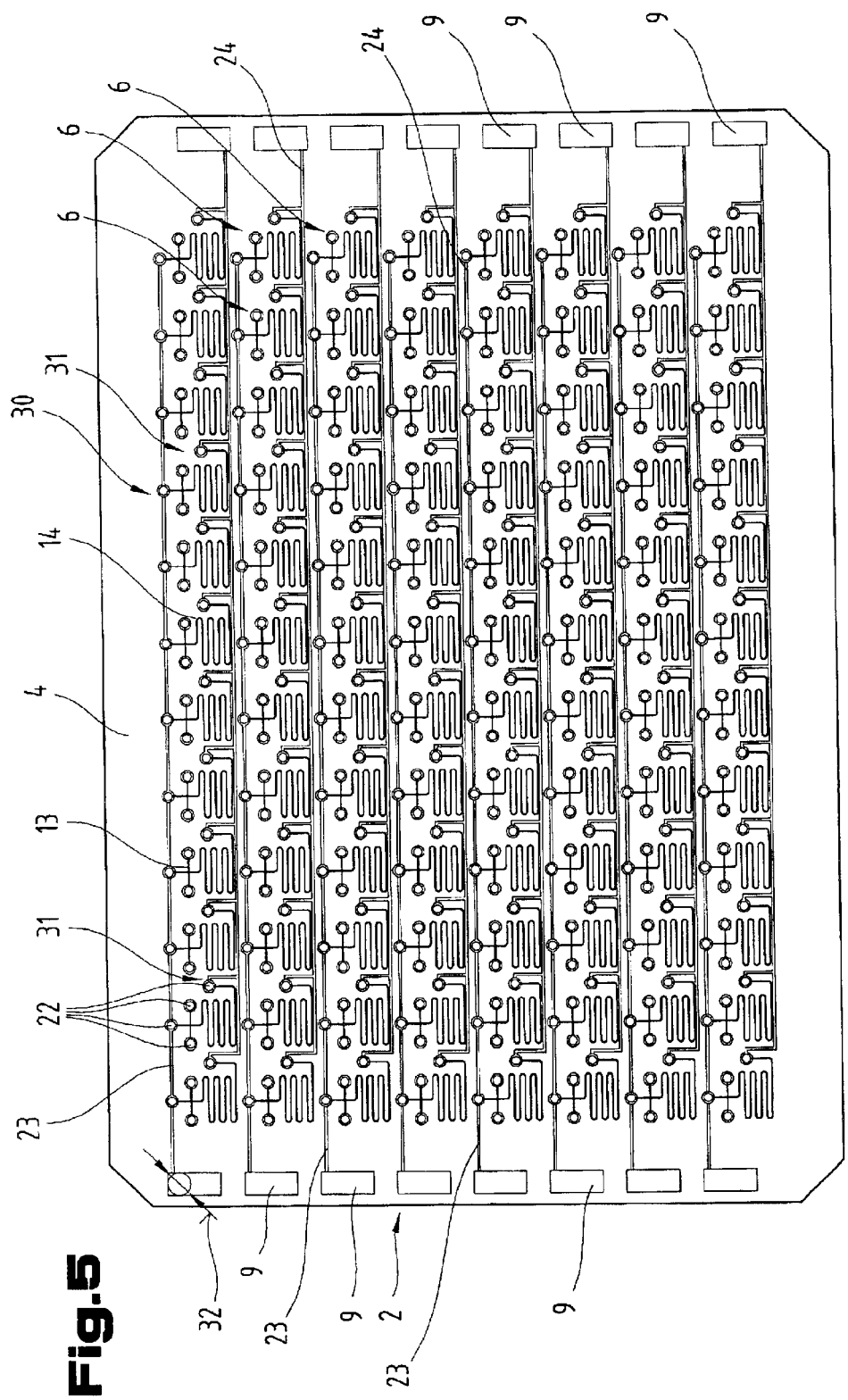

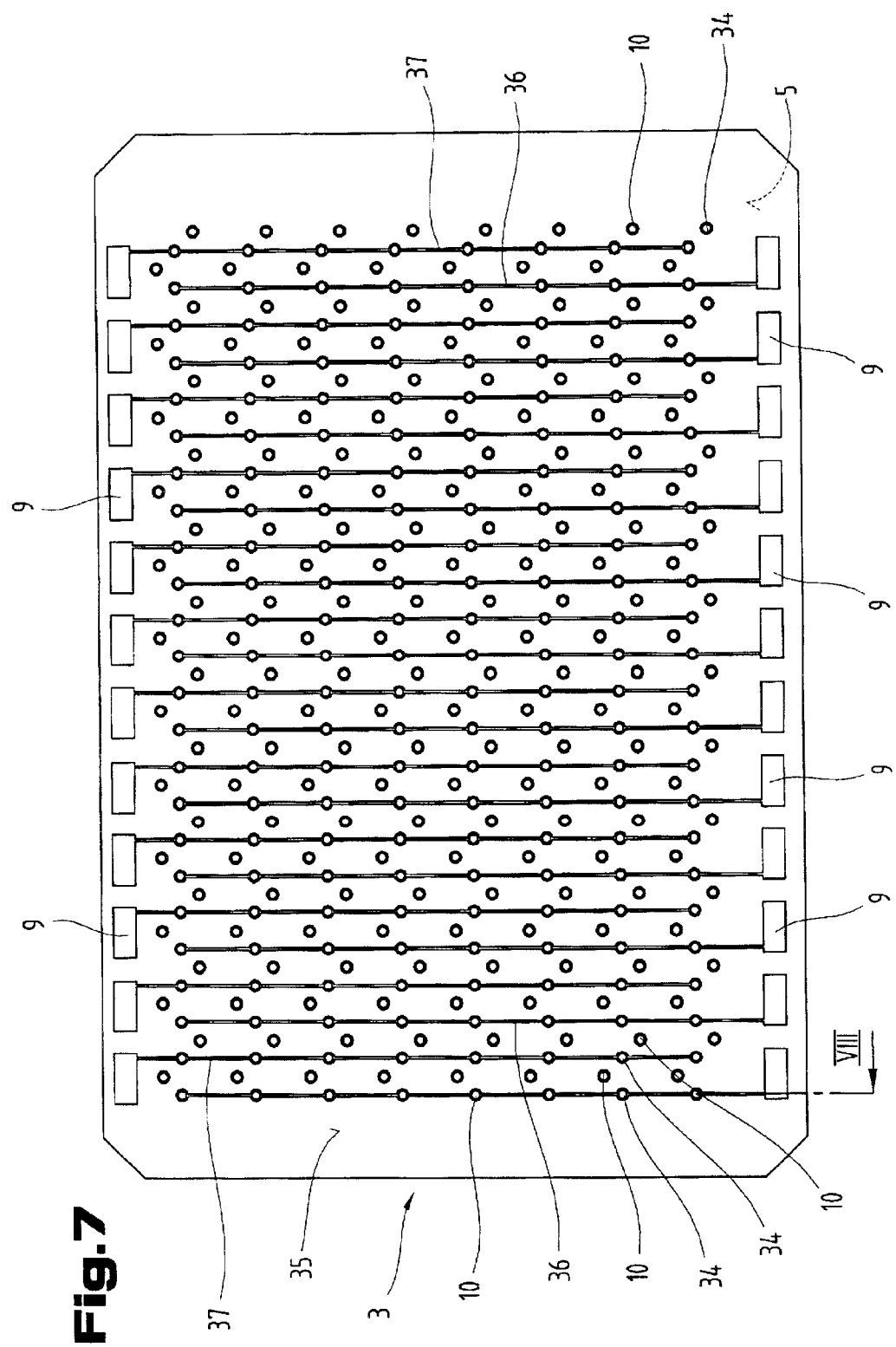

ANALYSIS SYSTEM

FIELD OF THE INVENTION

The invention relates to an analysis system comprising a main body with a surface, at least one analysis unit, consisting of at least two reservoirs placed in flow connection by at least one passage, being disposed in the main body.

PRIOR ART

Systems made up of micro-passages and known as microfluid systems find applications in micro-system technology in the form of miniaturised chemical or biochemical analysis systems. Microanalysis systems are used in the specific fields of research into agents, chemical diagnosis, genome analysis, environmental analysis and combined chemistry, for example. The specific feature which they offer is that they allow only very small quantities of fluid to be conveyed and manipulated. Other fields of application include microreactors in which chemical reactions take place, for example, or microtitre plates.

In the case of capillary electrophoresis, a sample is placed in a thin capillary, the width of which is in the order of several tens of $\mu$m, and is broken down into its different components under the influence of an electric field and analysed.

Both glass and plastics are used to manufacture microstructures. WO 98/45693 A1 discloses a method of manufacturing micro-passage structures, for example. The micro-passage structures are provided by means of a base plate and a cover plate, the micro-passages being arranged in a flat surface of the base plate which is closed when a flat surface of the cover plate is placed on it. Openings through which the samples can be fed are provided in the cover plate at the ends of the micro-passages.

In order to be able to apply an electric field to the samples in the known micro-passage structures, it is necessary to insert electrodes through the openings at the ends of the micro-passages. The openings through which the samples have to be introduced and through which the electrodes also have to be inserted need to be correspondingly small, especially where a plurality of micro-passage structures is arranged on microtitre plates. However, this means that the mechanical control involved in introducing the electrodes needs to be all the more accurate. This process can hamper the process of making contacts and thereby impair operating safety.

OBJECTIVE AND ADVANTAGES OF THE INVENTION

Accordingly, it is an objective of the invention to propose an analysis system for conducting electrochemical or electrokinetic tests which is easier to operate.

This objective is achieved by the invention due to an analysis system comprising a main body with a surface, at least one analysis unit consisting of at least two reservoirs placed in flow connection by at least one passage being arranged in the main body, characterised in that two electrical conductors are disposed in the main body or on the surface, each having a first end region connected respectively to one of the at least two reservoirs, and each second end region of the conductor beings connected to a contact point on the surface of the main body or constituting this contact point. The advantage of this arrangement is that operating safety is increased because the electrical conductors and contact points are mounted on the main body of the analysis system and in particular because the contact points are mounted at a distance from the reservoirs of the analysis units so that the liquids or samples disposed in the reservoirs or passages will not be disturbed when electrodes are introduced into and removed from the reservoirs.

The main body of another embodiment of the analysis system comprises a base plate and a cover plate and the base plate and the cover plate are joined to one another by surfaces, which is of advantage because the passages and reservoirs forming the analysis unit can be made by providing recesses in one of the surfaces of the base and/or cover plate. Placing the base plate and cover plate against one another and joining them offers any easy means of closing the passages so that they can not be accessed from outside except by the reservoirs at their end regions.

In an improved embodiment in which the conductors are connected to the main body by a connection method selected from a group of connection methods consisting of bonding, vapour deposition, insertion in recesses and integral moulding, the analysis units can advantageously be made compact in design and in particular the risk of damaging the conductors can be minimised.

In another embodiment of the analysis system in which at least a part of a reservoir floor is provided in the form of the conductor or at least a part of the reservoir wall is provided in the form of the conductor, an advantage is gained because the liquid disposed in the reservoir is in contact with a sufficiently large wettable surface of the conductor to enable the current to be passed between it and the conductor, which means that contact resistance can be kept low. Having a sufficiently large conducting surface for the current to pass is an advantage given the small dimensions of the reservoirs in micro-passage structures.

Particular advantages are to be gained from another embodiment of the analysis system in which the first end region of the conductor is designed as an electrode extending between the reservoir floor and an underside of the base plate, since this allows the analysis units to be made in a simple structure. Because the electrodes run from the reservoir floor to the underside of the base plate, all conductors and their contact points can be arranged exclusively on the underside of the base plate. If the base plate is a plastics injection moulded component, the electrodes, conductors and their contact points can be made as integral components and these components placed in an injection mould so that the base plate can be made complete with electrical conductors in a single processing step.

In another design of the analysis system in which the contact points are designed to have a contact surface with a specific internal diameter and the reservoirs to have an opening with a specific internal diameter and the internal diameter of the contact surface is larger than the internal diameter of the reservoir openings, there will advantageously be much fewer errors in making contact with the contact points when voltage is applied than would normally be the case with microanalysis systems in which the reservoirs have very small openings.

Another embodiment of the analysis system in which the contact points are arranged at one common end region of the main body only offers advantages because appropriate adapters can be used to make contact with the contact points and these will have to be introduced into the analysis system from one side only.

In another embodiment of the analysis system, the conductors are made from a material selected from a group of materials consisting of metal, electrically conductive plastics, conductive paste and electrically conductive varnish, the advantage of which is that analysis systems can be produced whose electrical conductors will be sufficiently electrically conductive to enable capillary electrophoresis testing to be carried out.

Advantages are also to be had from other embodiments in which the main body is designed to the standard size of a microtitre plate or several analysis units are disposed in the layout used as standard for a microtitre plate or a predeterminable number of analysis units is provided, this number being selected from a group consisting of the numbers solving the mathematical formula $3 \times 2^N$ where N is a whole number, or if 96 analysis units are provided, since these options will allow them to be used with standard automated equipment commonly used for microtitre plates to conduct corresponding analyses. This means that the reservoirs can be filled with samples using standardised pipette systems, for example.

If using embodiments of the analysis system in which the passage is designed as a micro-passage and the analysis unit is designed to have four reservoirs and if each two reservoirs are connected respectively to a passage and the two passages are connected respectively by a common intersecting region, there is the advantage firstly that very homogeneous flow conditions will prevail in the micro-passages due to capillary action and secondly a very small volume of a few 100 pl can be separated off in the intersecting region of the two passages for conducting capillary electrophoresis tests.

The embodiment of the analysis system in which four reservoirs are arranged in the standard layout used for a microtitre plate offers an advantage in that the standard equipment used to automate processing of microtitre plates can be used.

In accordance with another embodiment of the analysis system, a row width of the four reservoirs is the same as a half value of a row width of the analysis units, the advantage of which is that the reservoirs will be uniformly distributed on the analysis system, i.e. arranged with a maximum spacing between two immediately adjacent reservoirs.

Also of advantage is an embodiment of the analysis system in which the base plate and the cover plate are made from a plastics material, the plastics being selected from a group consisting of polymethacrylate, polycarbonate, polystyrene, polysulphone and cyclo-olefin copolymer, since these can be used to make a transparent main body for analysis systems, enabling the reactions in the passages of the analysis units to be detected.

Another embodiment of the analysis system has a base plate or cover plate which is at least partially opaque, which offers the advantage of being able to avoid any parasitic light when detecting fluorescent elements of the samples.

Finally, advantages are to be had from another embodiment of the analysis system in which the at least one passage is provided by means of recesses in at least one of the surfaces of the base plate and the cover plate is joined to at least the part of the surfaces of the base or cover plate immediately surrounding the reservoirs and passages by a joining method which affords a fluid-tight seal, the joining method being selected from a group consisting of bonding, applying polymerisable bonding agents, adhesion by temporary treatment with a solvent, heat sealing, ultrasonic welding and laser welding, since this will produce unimpaired homogeneous flow conditions in the passages.

BRIEF DESCRIPTION OF THE DRAWINGS

The invention will be described in more detail with reference to the embodiments illustrated as examples in the appended drawings.

Of these:

FIG. 2 is a head-on view of the analysis system illustrated in FIG. 1;

FIG. 3 is a diagram illustrating the operating principle of the analysis unit;

FIG. 4 is a section through the analysis system illustrated in FIG. 1;

FIG. 5 shows the base plate;

FIG. 6 is a section through an analysis system of the type illustrated in FIG. 1, showing a contact point;

FIG. 7 shows the cover plate;

DETAILED DESCRIPTION

Figure 1:
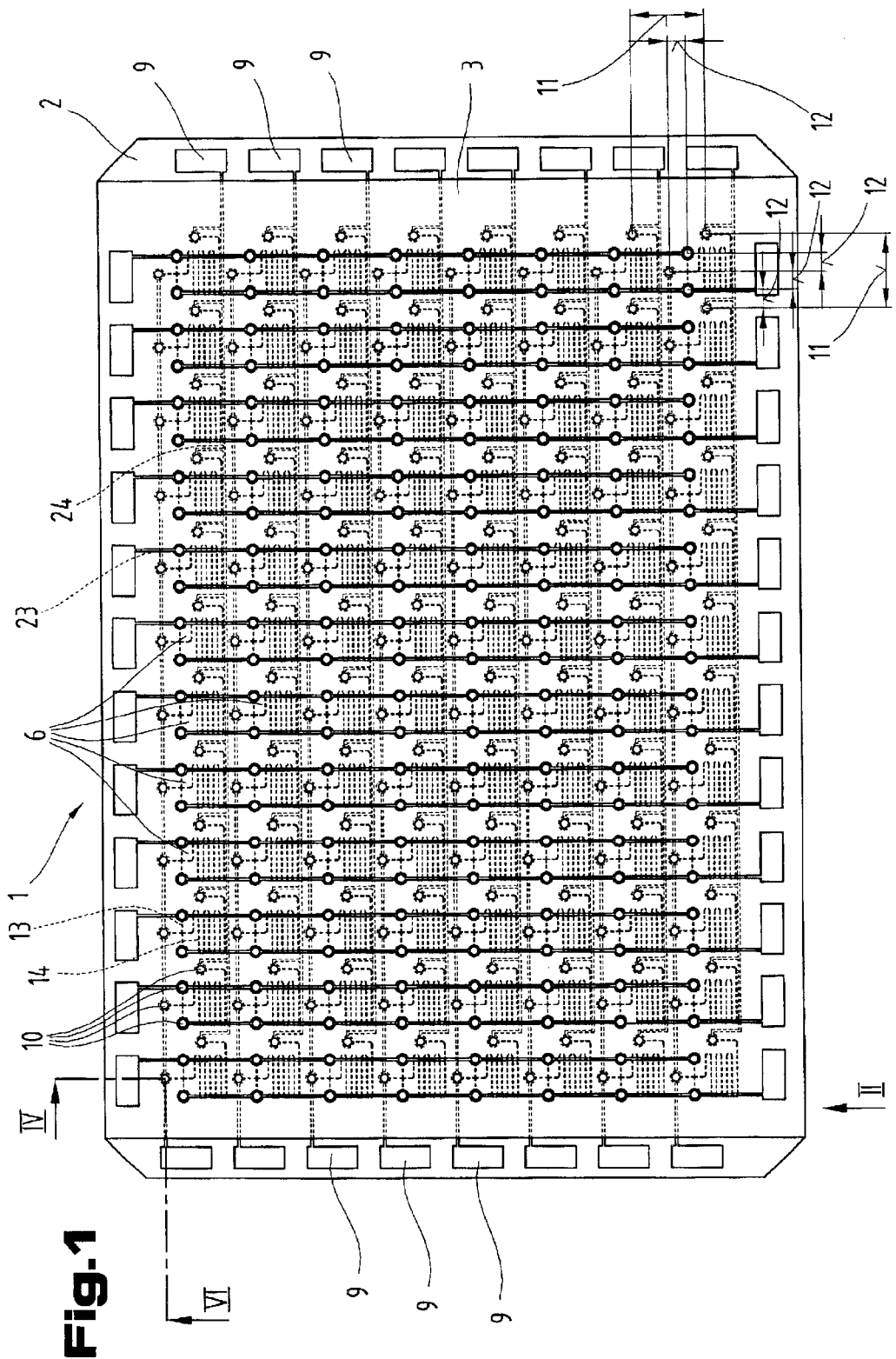
FIG. 1 shows an analysis system consisting of a base plate and a cover plate.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc, relate to the drawing specifically being described and can be transposed in terms of meaning to a new position when another position is being described. Individual features or combinations of features from the different embodiments illustrated and described may be construed as independent inventive solutions or solutions proposed by the invention in their own right.

FIGS. 1 and 2 illustrate an analysis system as proposed by the invention, consisting of a plate-design main body 1. The main body 1 is made up of a base plate 2 and a cover plate 3, which are joined to one another at a surface 4 of the base plate 2 and a surface 5 of the cover plate 3.

In total, 96 analysis units 6 (partially illustrated by broken lines) are provided in the main body 1 formed by the base plate 2 and cover plate 3. The analysis units 6 are used for running electrochemical tests or reactions. In order to provide the analysis units 6 with electrical contacts, several contact points 9 are provided on the surface 4 of the base plate 2. Each of the analysis units 6 also has four reservoirs 10, by means of which the samples and buffer solutions can be introduced. The reservoirs 10 are provided in the form of cylindrical holes in the cover plate 3.

The external dimensions of the main body 1 of the analysis system conform to a size used as standard for a microtitre plate. Accordingly, the analysis units 6 are also arranged in a rectangular pattern conforming to the standard pattern of a microtitre plate with 96 units. A row width 11, i.e. the lateral spacing between the analysis units 6, is respectively 9 mm in the direction of the longitudinal extension of the main body 1 and perpendicular thereto. The reservoirs 10 are laid out in a rectangular pattern with a row width 12 of 2.25 mm, i.e. the row width 12 corresponds to a quarter of the row width 11 of the analysis units 6 and hence a standard layout of a microtitre plate with 1536 units.

Clearly, the analysis system proposed by the invention could also be made with a different number of analysis units 6 in a main body 1. However, it is of advantage to use designs with a rectangular pattern, in particular having a number corresponding to the numbers used for microtitre plates, i.e. the number is derived from the mathematical formula $3 \times 2^N$, N being a whole number.

In another possible embodiment, the main body 1 and the base plate 2 or the cover plate 3 may be integrally joined to a frame at its or their peripheral regions. The frame is advantageously the same shape as that used for standardised microtitre plates.

The base plate 2 and the cover plate 3 are advantageously made from polymethacrylate. However, other plastics which may be used are polycarbonate, polystyrene, polysulphone and cyclo-olefin copolymer. However, it is of advantage if at least one of the two plates is made from a transparent plastics, since this will enable the reactions in the analysis units 6 to be detected from the outside.

The surfaces 4, 5 of the base plate 2 and the cover plate 3 are joined by methods such as bonding, applying polymerisable binding agents, heat sealing, ultrasonic welding or laser welding, for example. It is of advantage if the base plate 2 and cover plate 3 are joined by briefly treating them with a solvent so that the surfaces 4, 5 bite slightly, enabling them to be firmly joined to one another when the base plate 2 and cover plate 3 are placed together.

FIG. 3 is a diagram illustrating the operating principle of an analysis unit 6, of which there is a plurality in the main body 1 (FIG. 1). The analysis unit 6 consists of four reservoirs 10, two reservoirs 10 being in flow connection with one another by means of a passage 13 and two other reservoirs 10 by means of a passage 14. The passage 13 and the passage 14 intersect one another in a common intersection region.

The two passages 13 and 14 are designed as what are known as micro-passages and have a width 16 of 200 μm and a depth 17 (FIG. 4) of 100 μm. It is of advantage if the cross sections of the passages 13, 14 have a width 16 in a range of smaller than 200 μm and a depth 17 in a range smaller than 100 μm. The meandering part of the passage 14 between the reservoir 10 disposed at its end region and the intersection region 15 is approximately 40 mm in length.

An analysis unit 6 of this type is suitable for conducting tests using capillary electrophoresis. To this end, in a first step, a buffer solution or a gel is firstly introduced into a reservoir 10, the passages 13 and 14 and the reservoirs 10 being filled due to the capillary action at the ends of the passages 13 and 14. One of the two reservoirs 10 joined to one another via the passage 13 is then filled with the sample which, when a voltage is applied to the two reservoirs 10 connected to one another by the passage 13, is conveyed on towards the intersection region 15. In a second step, as soon as the greater part of the passage 13 but in any case the intersection region 15 is filled with the sample fluid, a voltage is applied between the two reservoirs 10 connected to one another by the passage 14, causing the volume of sample located in the intersection region, which will be approximately 500 pl, to move in the direction of the meandering part of the passage 14.

Depending on the different electric charge and the different size of the molecules contained in the sample, the different constituents of the sample are increasingly separated the farther away it moves from the intersection region 15 as it travels through the passage 14. Depending on the different molecule sizes and the different electrical charges of the different sample elements, their motion in the buffer solution or gel will vary and different sample elements will follow different courses over the same period of time in spite of applying a same electric voltage. The different elements of the sample which split off along the length of the passage 14 can be measured using an appropriate detection method and the elements of the sample identified.

FIG. 4 illustrates a section of an analysis system of the type illustrated in FIG. 1. The main body 1 of the analysis system consists of the base plate 2 and the cover plate 3, the base plate 2 having a thickness 20 of approximately 2 mm and the cover plate 3 also being of a thickness 21 of approximately 2 mm. Advantageously, the thicknesses 20, 21 are in a range of less than 2 mm, preferably in a range of less than 1 mm. Disposed in the cover plate 3 is a reservoir 10, provided as a cylindrical hole. The passages 13 and 14, having a depth 17 of 50 μm, are provided in the surface 4 of the base plate 2. At the end regions of the passages 13 and 14 are adjoining reservoir floors 22, which are also of the depth 17. The reservoirs 10 are therefore in flow connection with the passages 13, 14. The passages 13 and 14 and the reservoir floors 22 in the surface 4 are made by stamping with an appropriately designed punch at high temperature. Alternatively, they may also be made by other methods, for example injection moulding or removing the material by laser.

The base plate 2 and the cover plate 3 are permanently joined to one another by their surfaces 4 and 5, in which case at least parts of the surfaces 4 and 5 of the base plate and cover plate immediately surrounding the reservoirs and the passages are joined to one another in a fluid-tight seal. Liquids introduced into the reservoirs 10 or reservoir floors 22 and the passages 13 and 14 can not therefore penetrate the two surfaces 4 and 5 placed one against the other. This avoids disrupting the homogeneity of the flow conditions in the passages 13 and 14. The two surfaces 4 and 5 are connected by the methods mentioned in the part of the description given with reference to FIGS. 1 and 2.

The passages 13 and 14 may clearly also be provided in the surface 5 of the cover plate 3 or alternatively partly in the surface 4 of the base plate 2 and partly in the surface 5 of the cover plate 3. The fact that analysis units 6 are arranged in the main body 1 does not however mean that the passages 13 and 14 must be provided exclusively in the interior of the main body 1. The passages 13 and 14 could also be provided in the form of recesses in an external surface of the main body 1.

FIG. 5 illustrates the base plate 2. Several passages 13 and 14 and reservoir floors 22 belonging to analysis units 6 are arranged in a rectangular pattern in the surface 4 of the base plate 2, as described in relation to FIGS. 3 and 4. In order to be able to apply an electric voltage between the two reservoir floors 22 in the end regions of the passage 14, electrical conductors 23 and electrical conductors 24 are mounted on the surface 4. A first end region 30 of the conductor 23 is connected on the surface 4 of the base plate 2 by means of one the contact points 9 at its second end region. Similarly, the first end region 31 of the conductor 24 on the reservoir floor 22 of the second end of the passage 14 is connected to another contact point 9. Accordingly, at least a part of the reservoir floor 22 is provided in the form of the conductor 23 or 24.

In the embodiment illustrated as an example here, several reservoir floors of the same type, i.e. reservoir floors 22 in the end region of the short part of the passage 14 of analysis units 6 in a row are electrically connected respectively to a common contact point 9. The same applies for the reservoir bases 22 in the end region of the longer part of the passage 14, which are connected respectively in a row of analysis units 6 to the same conductor 24 via a common contact point 9.

The conductors 23 and 24 and the contact points 9 are preferably applied to the surface 4 of the base plate 2 by vapour depositing gold using appropriate shadow masks. Accordingly, a first end region of each conductor 23 and 24 is connected to a reservoir 10 and each second end region of the conductor 23 and 24 constitutes a respective contact point 9. However, it would also be possible to adhere conductor tracks onto the surface 4 or fit them in matching recesses. Another option would be to place ready-formed conductor tracks in injection moulds and mould them to produce corresponding injection moulded components.

The most suitable materials for the conductors are primarily metals, e.g. gold or platinum, or alternatively other electrically conductive materials such as electrically conductive plastics, conductive pastes or electrically conductive varnishes.

FIG. 6 shows a section through an analysis device with a contact point 9 as illustrated in FIG. 1. The end region 30 of the conductor 23 provides an electrical connection between the reservoir 10 and the contact point 9 on the surface 4 of the base plate 2, i.e. a contact point 9 on a surface of the main body.

An internal diameter 32 of the contact surface of the contact point 9 is substantially larger than an internal diameter 33 of an opening 34 of the reservoir 10. Consequently, it is significantly easier to apply the electric voltage to the reservoir 10. Compared with introducing electrodes into the reservoirs 10 through the openings 34, this means that applying electrodes to the contact points 9 will not require such a high degree of mechanical accuracy. To make contact with a contact, the internal diameter 32, 33 of the contact surface is effectively the decisive value constituting the likelihood of errors in the process of making contact. Mounting electrical conductors on the main body 1 therefore makes handling of the analysis systems easier, thereby increasing operating safety, since making contact with the contact points 9 requires less mechanical precision.

FIG. 7 depicts the cover plate 3, showing a top face 35, i.e. the side of the cover plate 3 remote from the surface 5. Only the openings 34 of the reservoirs 10 are visible on the top face 35 of the analysis systems.

Conductors 36 and conductors 37 are mounted on the top face 35 of the cover plate 3, each being electrically connected to contact points 9. These conductors 36 and 37 provide the electrical contact for the reservoirs 10, which are connected to one another by means of the passage 13 (not illustrated).

Figure 8:
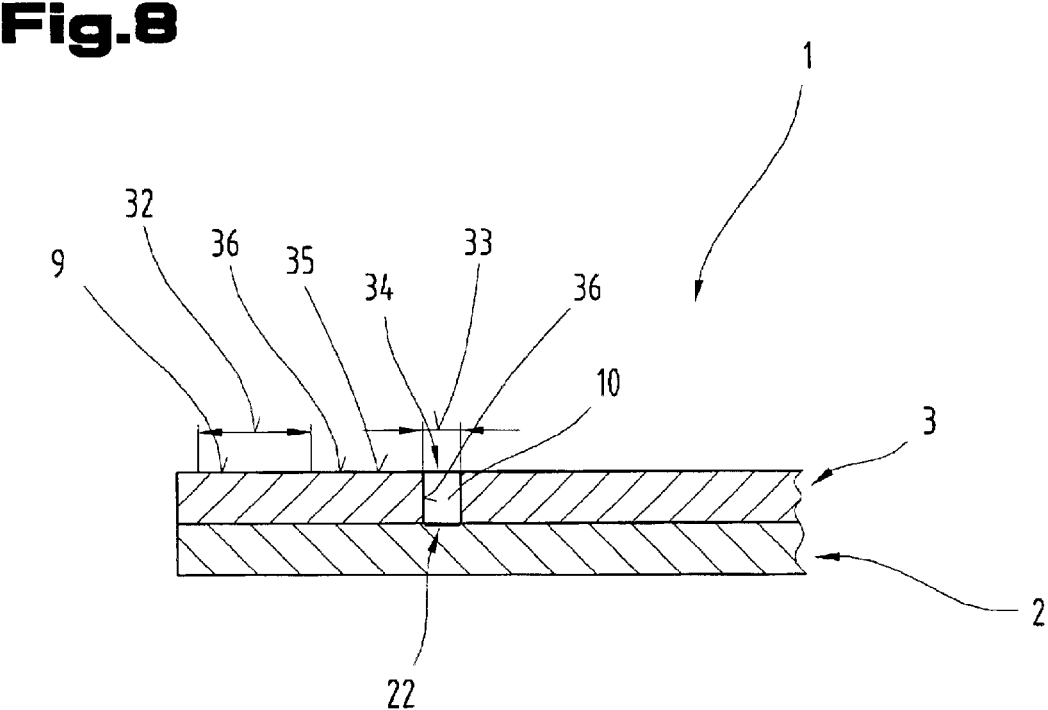
FIG. 8 is a section through an analysis system showing a contact point and conductors on the top face of the cover plate illustrated in FIG. 1.

FIG. 8 illustrates a section of an analysis system with a contact point 9 and conductors 36 on the top face 35 of the cover plate 3 illustrated in FIG. 1. The electrical conductor 36 connects the reservoir 10 to the contact point 9. Accordingly, the electrical conductor 36 extends from the top face 35 of the cover plate 3 through the opening 34 down into the reservoir 10 and along its walls. Consequently, at least a part of the reservoir wall serves as a conductor 36.

What is meant by part of the wall being used to form a conductor and part of the reservoir floor constituting the conductor (FIGS. 5 and 6) is literally that the reservoir wall or the reservoir floor is coated with a conductor.

Figure 9:
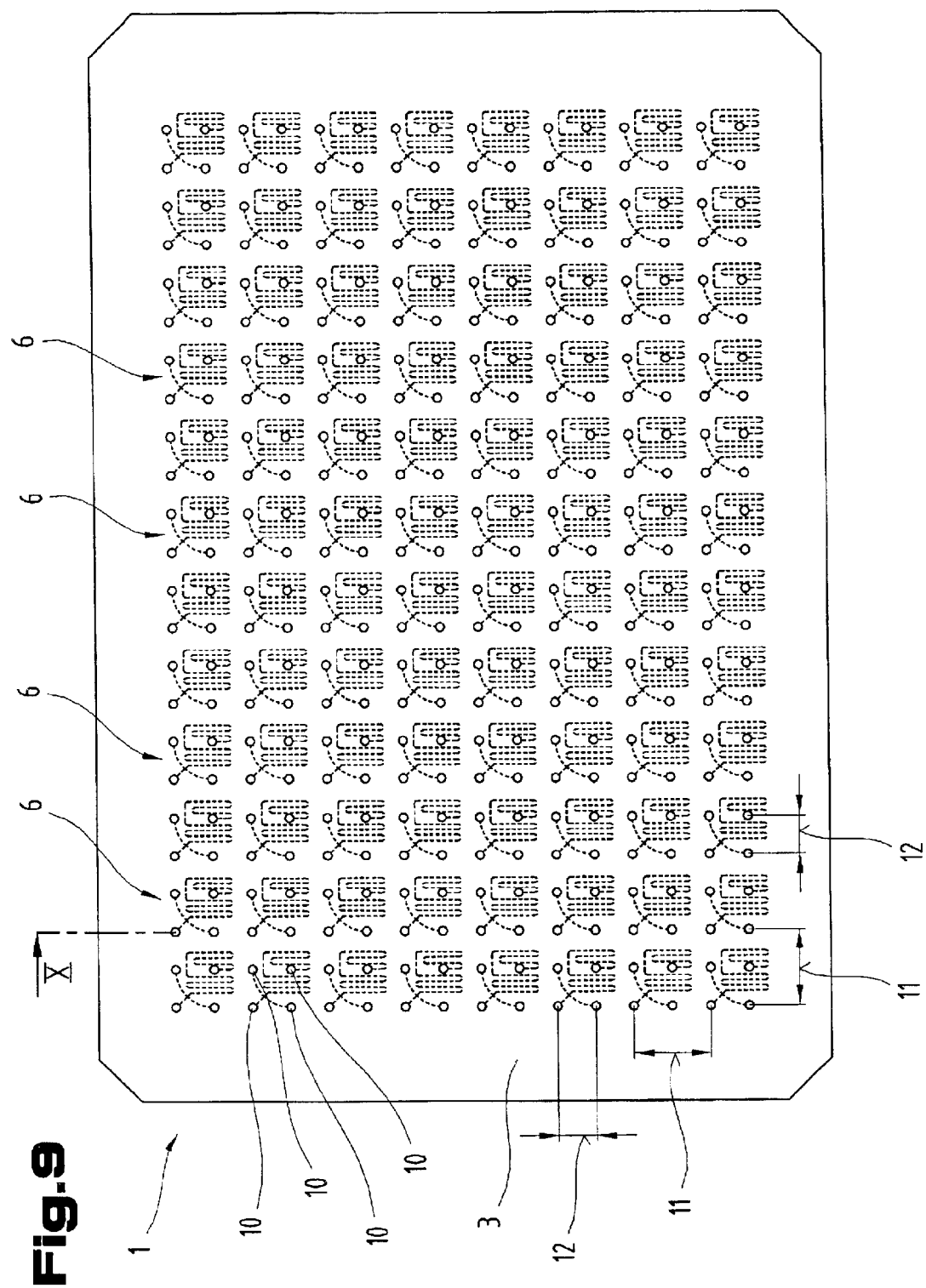
FIG. 9 illustrates an example of an embodiment of an analysis system with reservoirs laid out in a square pattern.

FIG. 9 illustrates another embodiment of an analysis device with reservoirs 10 laid out in a square pattern. The analysis units 6 (partially illustrated by broken lines) belonging to the reservoirs 10, of which there are 96 altogether, are laid out in a square pattern in the cover plate 3 of the main body 1 of the analysis system. A row width 12 of the reservoirs 10 is the same as a half value of a row width 11 of the analysis units 6. The analysis units 6 and the reservoirs 10 are respectively arranged in a layout of the standard type used for microtitre plates. In the analysis system illustrated, the row width 11 is 9 mm in the direction of longitudinal extension of the main body 1 and perpendicular thereto. The row width 12 of the reservoirs 10 is 4.5 mm.

In the layout of the reservoirs 10 described above, the distance of a reservoir 10 from the respective immediately adjacent reservoir 10 is advantageously of the maximum possible value. When filling the reservoirs 10 with sample fluid, the risk of the sample fluid overflowing into an adjacent reservoir 10 is reduced to a minimum.

Figure 10:
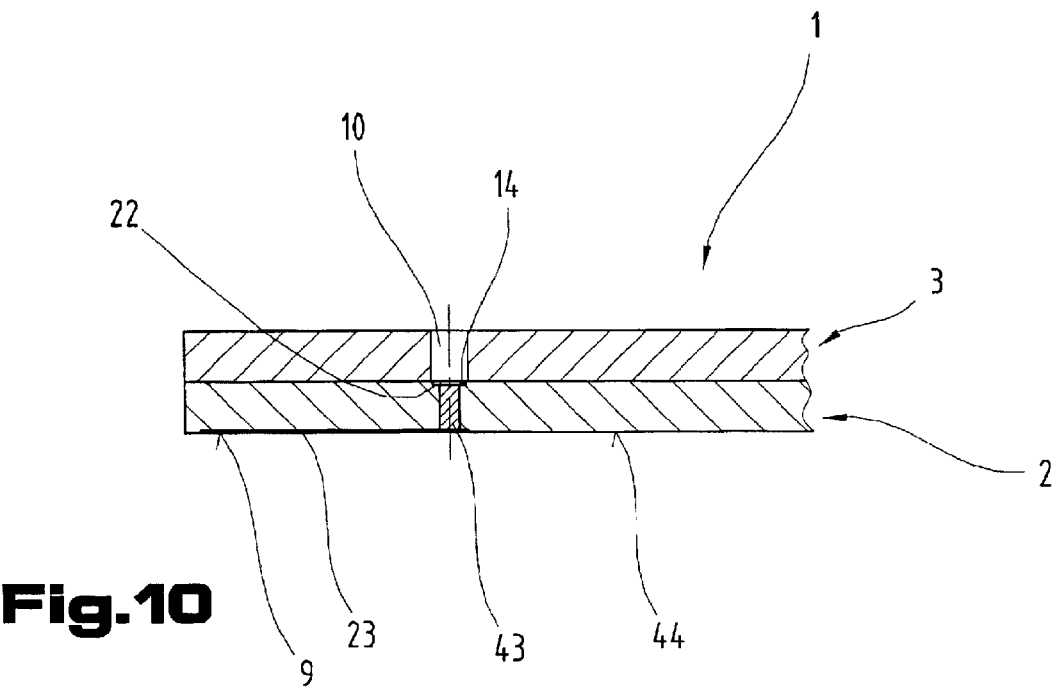
FIG. 10 is a section through an analysis system of the type illustrated in FIG. 9.

FIG. 10 illustrates a section of an analysis device of the type illustrated in FIG. 9. In this case, the first end region by means of which the conductor 23 is electrically connected to the reservoir 10 or reservoir floor 22 is provided in the form of an electrode 43. Accordingly, the electrode 43 extends between the reservoir floor 22 and an underside 44 of the base plate 2. Because the end regions of the conductors 23 and the conductors 24, 36, 37 (not illustrated) are designed as electrodes 43 extending between the reservoir floors 22 and the underside 44 of the base plate 2, the conductors 23, 24; 36, 37 may advantageously be disposed on the underside 44 of the base plate 2.

The conductors 23, 24; 36, 37, contact points 9 and electrodes 43 are preferably designed as integral structures so that they can advantageously be moulded into the base plate 2 in an injection moulding process.

Figure 11:
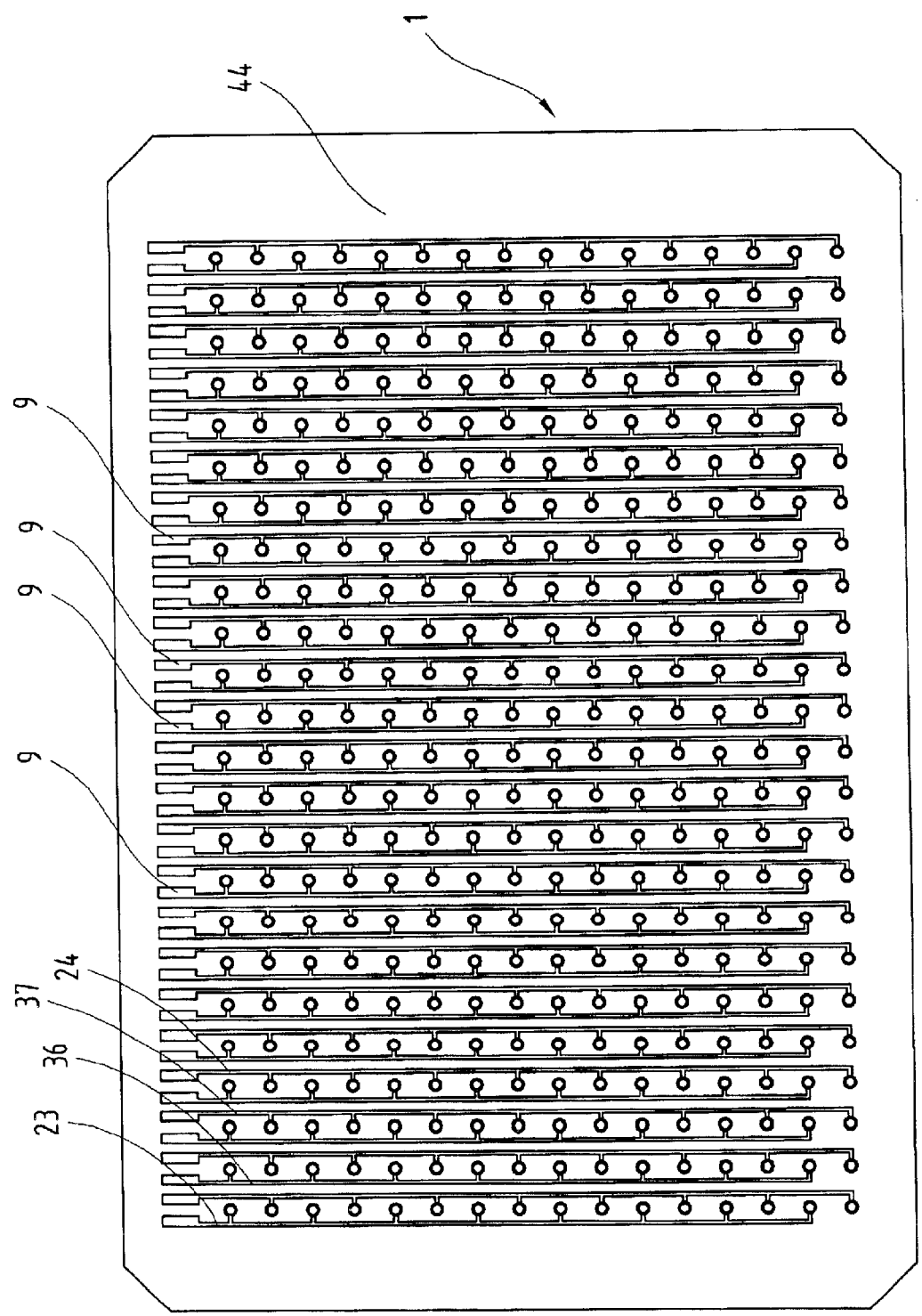
FIG. 11 shows an underside of an analysis system of the type illustrated in FIG. 9.

FIG. 11 illustrates an underside of the analysis system illustrated in FIG. 9. The conductors 23, 24 and 36, 37 of several analysis units 6 (not illustrated) lead to the same respective contact point 9. The contact points 9 are therefore advantageously at a common end region of the main body 1. However, the contact points 9 could alternatively be arranged at different end regions of the main body 1.

In an alternative embodiment of an analysis system, other layouts of the conductors, such as described with reference to FIGS. 5 and 8, could be combined with the arrangement described in relation to FIGS. 10 and 11. In other words, a proportion of the conductors may be arranged on the surface 4 of the base plate 2 (FIG. 5) or on the top face 35 of the cover plate 3 (FIGS. 7 and 8) whilst another proportion of the conductors may run along the underside 44 of the base plate 2.

Figure 12:
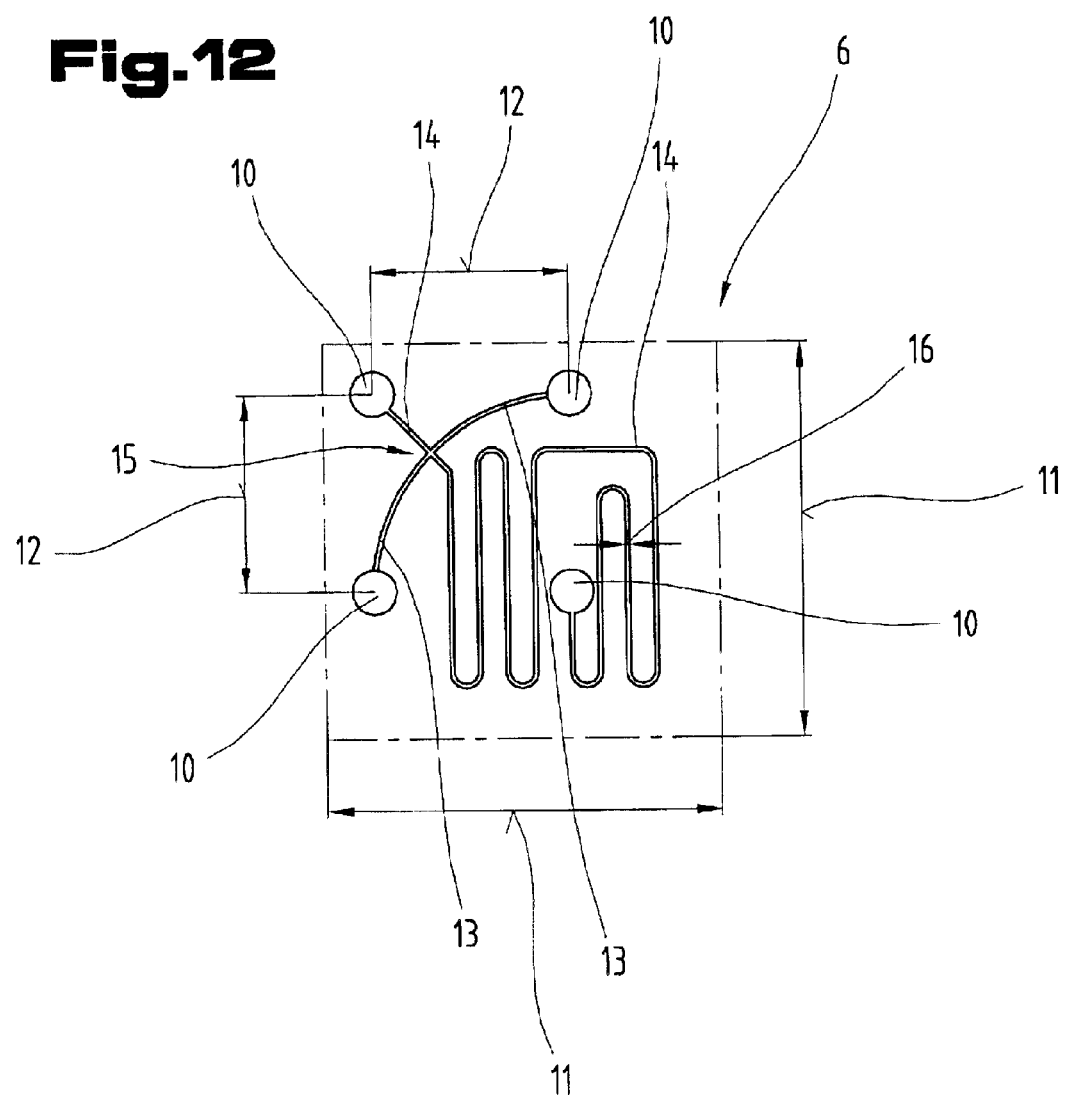
FIG. 12 is a diagram illustrating the operating principle of the analysis system illustrated in FIG. 9.

FIG. 12 is an operating diagram of an analysis system as illustrated in FIG. 9. The layout of the reservoirs 10 is therefore that in which the row width 12 corresponds to half the value of the row values 11 of 9 mm. The cross section of the passages 13 and 14 is of the same design as that in the embodiment described with reference to FIGS. 3 and 4, i.e. the width 16 is 100 $\mu$m and the depth 17 (FIG. 10) is 50 $\mu$m. An analysis unit 6. of the type illustrated in FIG. 12, is also suitable for conducting tests using capillary electrophoresis.

Figure 13:
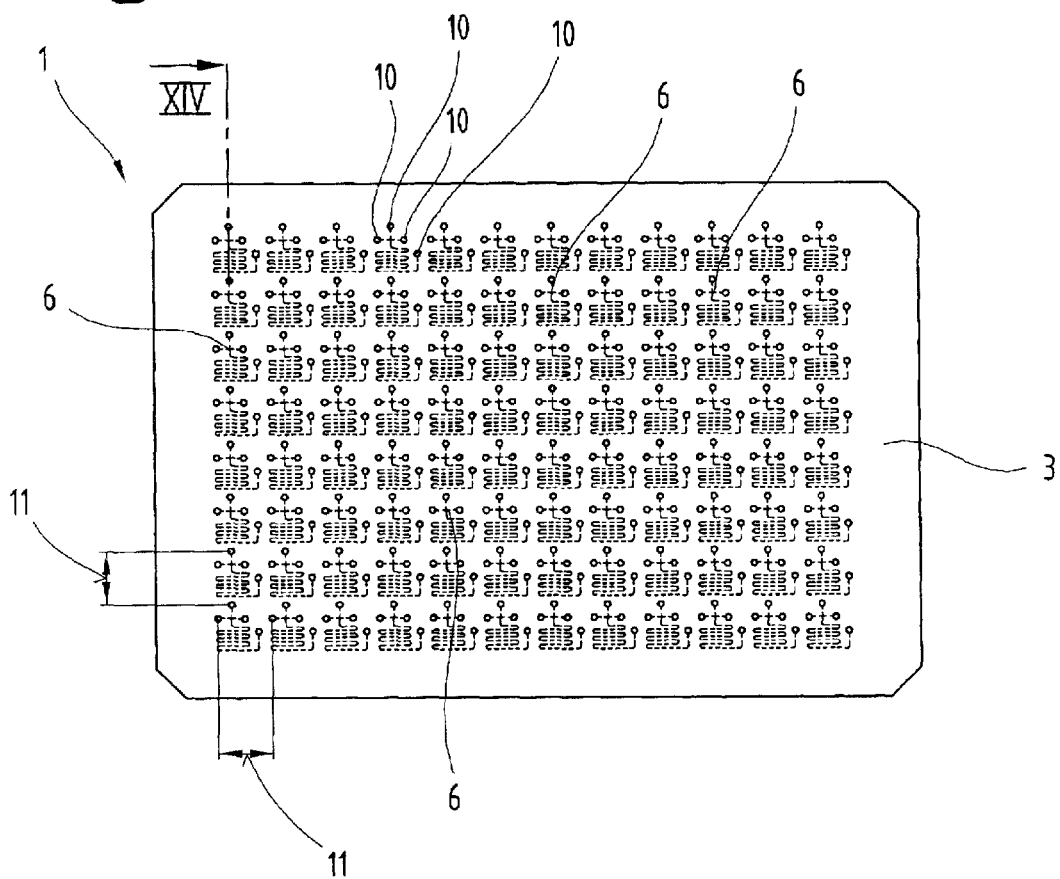
FIG. 13 is an analysis system without electrical conductors.
Figure 14:
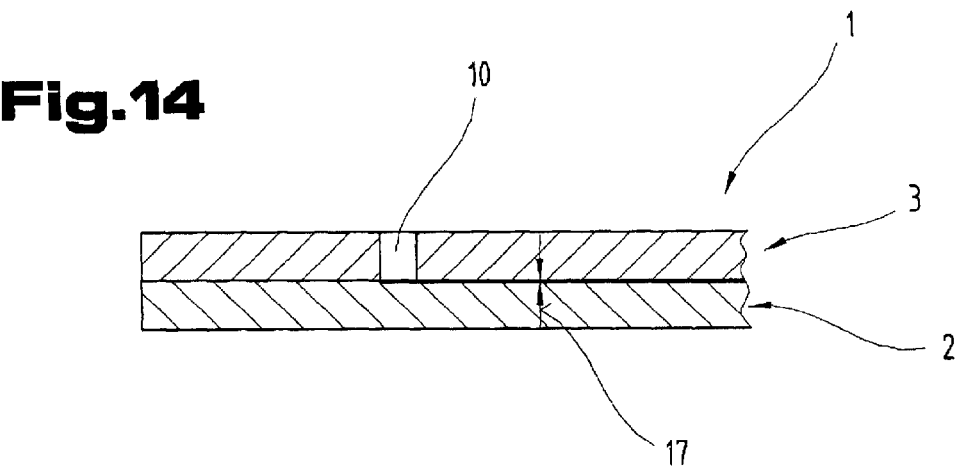
FIG. 14 is a section through an analysis system of the type illustrated in FIG. 13.

FIGS. 13 and 14 illustrate an analysis system without electrical conductors. The main body 1 consisting of the base plate 2 and the cover plate 3 is designed to the standard size of a microtitre plate. 96 analysis units 6 are provided in the main body 1, laid out in the pattern used as standard for a microtitre plate with a row width 11 of 9 mm in the direction of longitudinal extension of the main body 1 and perpendicular thereto. The layout of the analysis units 6 (partially illustrated by broken lines) corresponds to that described with reference to FIG. 3. Here too, the layout of the reservoirs 10 matches a standard layout of a microtitre plate with 1536 units.

In order to conduct tests using capillary electrophoresis with this embodiment of an analysis system, it is necessary to introduces electrodes into the reservoirs 10 from the outside in order to make the electrical contact.

For the sake of good order, it should finally be pointed out that in order to provide a clearer understanding of the structure of the analysis system, it and its constituent parts have been illustrated out of scale to a certain extent and/or on an enlarged and/or reduced scale.

The tasks underlying the independent inventive solutions can be found in the description.

Above all, the subject matter relating to the individual embodiments illustrated in FIGS. 1, 2, 3, 4, 5; 6, 7, 8; 9, 10, 11, 12; 13, 14 can be construed as independent solutions proposed by the invention. The tasks and solutions can be found in the detailed descriptions relating to these drawings.

List of Reference Numbers

1 Main body
2 Base plate
3 Cover plate
4 Surface
5 Surface
6 Analysis unit
7
8
9 Contact point
10 Reservoir
11 Row width
12 Row width
13 Passage
14 Passage
15 Intersection region
16 Width
17 Depth
18
19
20 Thickness
21 Thickness
22 Reservoir floor
23 Conductor
24 Conductor
25
26
27
28
29
30 End region
31 End region
32 Internal diameter
33 Internal diameter
34 Opening
35 Top face
36 Conductor
37 Conductor
38
39
40
41
42
43 Electrode
44 Underside

What is claimed is:

1. An analysis system comprising a main body having a surface and four peripheral regions bounding the surface, at least one analysis unit arranged in the main body, each analysis unit comprising two first reservoirs each defined by a reservoir floor and a reservoir wall, and two second reservoirs each defined by a reservoir floor and a reservoir wall, the two first reservoirs being in flow connection by a first passage and the two second reservoirs being in flow connection by a second passage, the first and second passages being connected to each other by a common intersection region; two electrical conductors arranged in the main body, each of the electrical conductors having a first end region and a second end region, a first one of the electrical conductors having the first end region connected to one of the first reservoirs and the second end region connected to or constituting a first contact point in at least one of the peripheral surface regions, and a second one of the electrical conductors having the first end region connected to one of the second reservoirs and the second end region connected to or constituting a second contact point in the peripheral surface region, at least part of the reservoir walls constitutes a part of the electrical conductors.

2. The analysis system of claim 1, wherein the main body comprises a base plate and a cover plate, the base plate being joined to the cover plate by surfaces thereof.

3. The analysis system of claim 2, wherein the base plate and the cover plate are made from plastics selected from the group consisting of polymethacrylate, polycarbonate, polystyrene, polysulphone and cycloolefin copolymer.

4. The analysis system of claim 2, wherein one of the plates is at least partially opaque.

5. The analysis system of claim 2, wherein the first end regions of the electrical conductors are electrodes extending between the reservoir floors and an underside of the base plate.

6. The analysis system of claim 2, wherein at least one of the passages is defined by recesses in at least one of the surfaces of the base plate and the cover plate, and at least those parts of the surfaces of the base plate and the cover plate immediately surrounding the reservoirs and the passages are joined in a fluid-tight seal by a joining method selected from the group consisting of bonding, applying polymerizable bonding agents, adhesion by temporary treatment with a solvent, heat sealing, ultrasonic welding and laser welding.

7. The analysis system of claim 1, wherein the electrical conductors are connected to the main body by a connection method selected from the group consisting of bonding, vapor deposition, insertion in recesses, and integral molding.

8. The analysis system of claim 1, wherein at least part of the reservoir floors constitutes a part of the electrical conductors.

9. The analysis system of claim 1, wherein each one of the contact points has a contact surface having a predetermined internal diameter and each one of the reservoirs has an opening having a predetermined internal diameter, the internal diameter of the contact surfaces being greater than the internal diameter of the openings.

10. The analysis system of claim 1, wherein each one of the contact points is disposed at one of the peripheral surface regions.

11. The analysis system of claim 1, wherein the electrical conductors are made from a material selected from the group consisting of metal, electrical conductive plastics, electrically conductive paste and electrically conductive varnish.

12. The analysis system of claim 1, wherein the main body has a disc constituting a standard for a microtitre plate.

13. The analysis system of claim 1, wherein several analysis units are arranged in a layout constituting a standard for a microtitre plate.

14. The analysis system of claim 1, wherein a predetermined number of the analysis units are arranged in the main body, the number being selected from the group of numbers solving the mathematical formula $3 \times 2^N$, N being a whole number.

15. The analysis system of claim 1, wherein 96 analysis units are arranged in the main body.

16. The analysis system of claim 1, wherein the passages are micro-passages.

17. The analysis system of claim 1, wherein the first and second reservoirs are laid out in a pattern constituting a standard for a microtitre plate.

18. The analysis system of claim 1, wherein a plurality of analysis units are arranged in parallel rows in the main body, the first and the second reservoirs are arranged in parallel rows, the rows of the first and second reservoirs having half the distance from each other and the rows of the analysis units.

* * * * *